(12) United States Patent  (10) Patent No.: US 7,550,442 B2
Huang et al.  (45) Date of Patent: Jun. 23, 2009

(54) NUCLEOSIDE ANALOG INHIBITORS OF REVERSE TRANSCRIPTASE

(75) Inventors: Raven H. Huang, Savoy, IL (US); Xianjun Liu, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 766 days.

(21) Appl. No.: 10/848,947

(22) Filed: May 19, 2004

(65) Prior Publication Data

US 2004/0235869 A1 Nov. 25, 2004

Related U.S. Application Data

(60) Provisional application No. 60/471,807, filed on May 20, 2003.

(51) Int. Cl.
A61K 31/7056 (2006.01)
A61K 31/706 (2006.01)
A61K 31/7064 (2006.01)
A61K 31/7068 (2006.01)
A61K 31/7072 (2006.01)
A61K 31/7076 (2006.01)
A61K 31/7078 (2006.01)

(52) U.S. Cl. ............................ 514/45; 514/46; 514/49; 514/50; 536/27.2; 536/27.3; 536/27.81; 536/28.53; 536/28.54

(58) Field of Classification Search ............. 514/263.28
See application file for complete search history.

(56) References Cited

U.S. PATENT DOCUMENTS

| 4,522,811 | A | 6/1985 | Eppstein et al. | |
|---|---|---|---|---|
| 5,602,240 | A * | 2/1997 | De Mesmaeker et al. | 536/22.1 |
| 7,081,449 | B2 * | 7/2006 | Pietrzkowski et al. | 514/45 |
| 7,285,658 | B2 * | 10/2007 | Cook et al. | 536/26.2 |
| 2002/0058635 | A1 * | 5/2002 | Averett | 514/43 |

FOREIGN PATENT DOCUMENTS

WO WO0203997 * 1/2002

OTHER PUBLICATIONS

Herdewijn et. al. J. Chem. Soc. Perkin. Trans. I, 1994, 249-255.*
Selma et. al. Tetrahedron, 52(32) 10785-10798, 1996.*
Ashwell et al., "The Synthesis of some Branched-Chain-Sugar Nucleoside Analogues" Nucleoc acids research (1987) vol. 15 No. 5, pp. 2157-2166.*
Averett, D.R. 1989. Anti-HIV compound assessment by two novel high capacity assays, J. Virol. Meth. 23:263-276.
Barre-Sinoussi, F., J.C. Chermann, F. Rey, M.T. Nugeyre, S. Chamaret, J. Gruest, C. Dauguet, C. Axler-Blin, F. Vezinet-Brun, C. Rouzioux, W. Rozenbaum, and L. Montagnier. 1983. Isolation of a T-lymphotropic retrovirus from a patient at risk for acquired immune deficiency syndrome (AIDS). Science. 220:868-71.

Beral, V., and R. Newton. 1998. Overview of the epidemiology of immunodeficiency-associated cancers. J Natl Cancer Inst Monogr: 1-6.

(Continued)

Primary Examiner—Shaojia Anna Jiang
Assistant Examiner—Eric S Olson
(74) Attorney, Agent, or Firm—Evan Law Group LLC

(57) ABSTRACT

Compounds of formula (XXIII), or pharmaceutically acceptable salts or esters thereof, are inhibitors of reverse transcriptase:

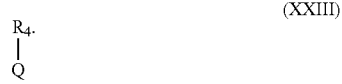

(XXIII)

$R_4$ is a nucleoside with Q substituting a 3' hydroxyl group, and Q is a moiety of formulas (XXIV)-(XXXII):

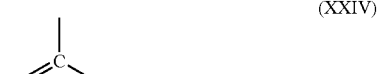

(XXIV)

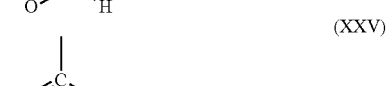

(XXV)

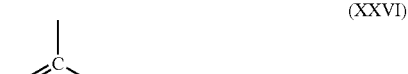

(XXVI)

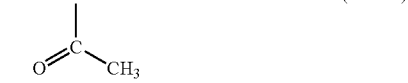

(XXVII)

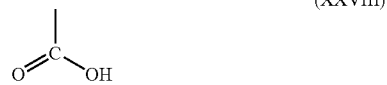

(XXVIII)

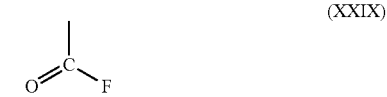

(XXIX)

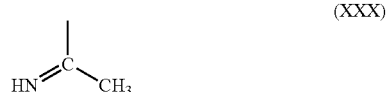

(XXX)

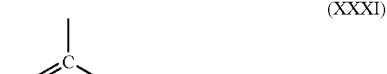

(XXXI)

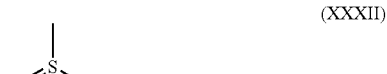

(XXXII)

7 Claims, 2 Drawing Sheets

OTHER PUBLICATIONS

Gallo, R.C., S.Z. Salahuddin, M. Popovic, G.M. Shearer, M. Kaplan, B.F. Haynes, T.J. Palker, R. Redfield, J. Oleske, B. Safai, and et al. 1984. Frequent detection and isolation of cytopathic retroviruses (HTLV-III) from patients with AIDS and at risk for AIDS. *Science.* 224:500-3.

Hossain, N., A. Papchikhin, N. Garg, I. Fedoriv and J. Chattopadhyaya. 1993. Synthesis of 2',3'-Dideoxy-3'-Nitro-2',3'-Didehydrothymidine. Its Use as a General Intermediate for the Preparation of Various 2',3'-Substituted Nucleosides. *Nucleosides & Nucleotides.* 12:499-528.

Huang, H., R. Chopra, G.L. Verdine, and S.C. Harrison. 1998. Structure of a covalently trapped catalytic complex of HIV-1 reverse transcriptase: implications for drug resistance. *Science.* 282:1669-75.

Huang, J.J., A. Rogouzeos and J.L. Rideout. 1995. A novel synthesis of 3'-deoxy-3'-nitrothymidine via nucleophilic substitution with nitrite anion. *J. Heterocyclic Chem.* 32:691-695.

Huang, P., D. Farquhar, and W. Plunkett. 1990. Selective action of 3'-azido-3'-deoxythymidine 5'-triphosphate on viral reverse transcriptases and human DNA polymerases. *J. Biol Chem.* 265:11914-8.

Lin, T.S., and W.R. Mancini. 1983. Synthesis and antineoplastic activity of 3'-azido and 3'-amino analogues of pyrimidine deoxyribonucleoside. *J Med Chem.* 26:544-8.

Palella, F.J., Jr., K.M. Delaney, A.C. Moorman, M.O. Loveless, J. Fuhrer, G.A. Satten, D.J. Aschman, and S.D. Holmberg. 1998. Declining morbidity and mortality among patients with advanced human immunodeficiency virus infection. HIV Outpatient Study Investigators. *N Engl J Med.* 338:853-60.

Prevention, C.f.D.C.a. 1992. Centers for Disease Control and Prevention 1993 revised classification system for HIV infection and expanded surveillance case definition for AIDS among adolescents and adults. Morb. Mort. Week Report. 42:1-18.

Wei, X., S.K. Ghosh, M.E. Taylor, V.A. Johnson, E.A. Emini, P. Deutsch, J.D. Lifson, S. Bonhoeffer, M.A. Nowak, B.H. Hahn, and et al. 1995. Viral dynamics in human immunodeficiency virus type 1 infection. Nature. 373:117-22.

Yu, D., et al., "Synthesis of 3'=Cyano-2',3'-dideoxyadenosine and 2',3'-Dideoxy-3'-formyladenosine", American Chemical Society, vol. 54, pp. 3240-3242, (1989).

Lin, T., et al., "Syntheses and Biological Evaluations of 3'-Deoxy-3'-Deoxy-3'-C-Branched-Chain-Substituted Nucleosides", J. Med. Chem., vol. 36, pp. 353-362, (1993).

* cited by examiner

*Primer is SEQ ID NO:2; template is SEQ ID NO:1

NUCLEOSIDE ANALOG INHIBITORS OF REVERSE TRANSCRIPTASE

RELATED APPLICATIONS

This application claims the benefit of U.S. Provisional Application No. 60/471,807 filed on May 20, 2003.

BACKGROUND

Acquired immune deficiency syndrome (AIDS) is caused by the human immunodeficiency virus (HIV), a retrovirus of the lentivirus family that was not discovered until the early 1980's. Knowing no boundaries, the virus has spread around the world to infect millions (Barre-Sinoussi et al., 1983; Gallo et al., 1984). HIV relentlessly destroys the immune system, the body's defense to invading pathogens. Those infected with HIV are susceptible to opportunistic infectious and neoplastic complications as a result of the inevitable manifestation of AIDS, thus succumbing to illness and death. The cost of the disease is incomprehensible; economic damages alone are staggering, but those for emotional and societal are beyond comprehension. The virus infects more victims every year, with little respite in sight, especially in undeveloped nations.

The virus not only weakens the barrier to opportunistic pathogen invasion, but also contributes to neoplastic complications. Through the suppression of the immune system, HIV facilitates the formation of several cancers, such as Kaposi's sarcoma (KS), non-Hodgkin's lymphomas (NHL) and cervical cancer (Prevention, 1992). HIV is thought to affect other cancers, such as Hodgkin's lymphomas, leiomyosarcoma, liver cancer, lung cancer, anal cancer, testicular cancer, oropharyngeal cancer, mieloma, and non-melanoma skin cancer (Beral and Newton, 1998).

When HIV infects a cell, it uses its reverse transcriptase (RT) to transcribe its RNA to DNA; the DNA then integrates into the host genome. This "proviral DNA" usurps cellular resources to cause the cell to produce additional HIV virions, which are then released from the cell. The HIV genome contains three major genes: env, gag, and pol. These genes encode the basic components of HIV. Env encodes the envelope precursor protein, gp160, that is protealyzed to 120 kd, producing the outer envelope glycoprotein gp120. Gp120 is responsible for tropism to CD4+ receptors; and transmembrane glycoprotein gp41, which catalyzes fusion of HIV to the membranes of the cell being infected. Gag encodes the matrix protein p17, the core capsid protein p24, and the nucleocapsid protein p7. Pol encodes various enzymes, including the reverse transcriptase p66, integrase p32, and protease p11.

Because RT is a necessary component of HIV proliferation, it has become a primary target for therapeutic attack. Several RT inhibitors are currently in use in the US (See Tables 1 and 3). Based on their mechanisms of action, RT inhibitors are divided into two groups: (1) non-nucleoside and (2) nucleoside analog inhibitors. The non-nucleoside inhibitors have diverse chemical structures, but all bind a hydrophobic pocket in RT that is adjacent to the polymerase active site. This binding is thought to reduce the enzymatic activity of RT through direct steric perturbations, inhibiting DNA replication. Because of the rapid appearance of drug resistance, non-nucleoside inhibitors are seldom used clinically (Wei et al., 1995).

Nucleoside analog inhibitors are pro-drugs and must be converted into the active form, the 5'-triphosphate, by cellular enzymes to be effective. Nucleoside analog inhibitors lack the 3'-hydroxyl groups required for DNA chain extension during reverse transcription. Incorporation of these molecules into the growing polynucleotide by RT causes premature chain termination, thereby inhibiting DNA replication.

In addition to the RT inhibitors, molecules that target the HIV protease (Table 2) substantially reduce the death rate (Palella et al., 1998). If either protease inhibitors or RT inhibitors are administered alone, HIV quickly mutates, becoming resistant to the drugs and compromising treatment. Combination therapy circumvents this problem by simultaneously administering multiple drugs. Such drug "cocktails" usually contain three inhibitors: one directed against protease and two against RTs. In some patients, this combinatorial weapon reduces the amount of virus in the body to an undetectable level; but this result is hardly universal. The battle against AIDS continues to rage and claim casualties.

Current battle plans to fight HIV infection have significant drawbacks. First, combination therapy is expensive, and the number of inhibitors, especially those of RTs, is limited. Second, drug administration is a life-long requirement: HIV levels increase upon arresting therapy. Third, a patient must obey a strict schedule of administration. If the strict schedule is not adhered to, viral strains simultaneously resistant to multiple drugs arise, again compromising therapy. Finally, economic considerations preclude treatment of those people without sufficient resources, especially in developing countries, where the largest population of HIV infected patients live.

TABLE 1

Nucleoside/nucleotide reverse transcriptase inhibitors (NRTIS)

| Drug | Adult dosing | Side effects[1] | Notes |
| --- | --- | --- | --- |
| Retrovir ® (AZT), by GlaxoSmithKline (Research Triangle Park, NC) | 300 mg × 2/day | Nausea; stomach discomfort; headache; insomnia; muscle wasting; anemia; neutropenia | |
| Epivir ® (3TC), by GlaxoSmithKline | 300 mg × 1/day or 150 mg × 2/day | Nausea | Also used to treat patients infected with the Hepatitis B Virus (HBV), but at a different dose. If dually infected, the HIV dosage is used. |
| Combivir ® (AZT + 3TC), by GlaxoSmithKline | 300 mg AZT + 150 mg 3TC × 2/day | Nausea; loss of appetite; headache; fatigue; stomach discomfort; muscle wasting anemia; neutropenia | |
| Trizivir ® | 300 mg AZT + 150 mg | Similar side effects to Retrovir (AZT), Epivir (3TC), | Subject must weigh |

TABLE 1-continued

Nucleoside/nucleotide reverse transcriptase inhibitors (NRTIS)

| Drug | Adult dosing | Side effects[1] | Notes |
|---|---|---|---|
| (AZT + 3TC + abacavir), by GlaxoSmithKline | 3TC + 300 mg abacavir × 2/day | and Ziagen (abacavir). | greater than 90 pounds (40 kg). |
| Ziagen ® (abacavir), by GlaxoSmithKline | 300 mg × 2/day | Nausea; vomiting; diarrhea; loss of appetite; insomnia Serious allergic reactions in about 3-5% of patients. | Take with or without food. |
| Videx ® (ddI): buffered versions, by Bristol-Myers Squibb (New York, NY) | 200 mg × 2/day or 400 mg × 1/day | Peripheral neuropathy; nausea; diarrhea; vomiting; headache; rash; pancreatitis. | Twice-daily dosing is more effective. Possible increased side effects if taken with tenofovir (Viread). |
| Videx ® EC (ddI): delayed-release capsules, by Bristol-Myers Squibb | 400 mg × 1/day; if subject weighs less than 133 lbs. (60 kg), then 250 mg × 1/day | Numbness, tingling, or pain in the hands or feet (peripheral neuropathy, seen in 15% of patients); nausea; diarrhea; vomiting; headache; rash; pancreatitis. Possible increased side effects if taken with tenofovir (Viread). | |
| Zerit ® (d4T), by Bristol-Myers Squibb | 40 mg every 12 hours | Peripheral neuropathy; nausea; diarrhea; vomiting; headache; rash; pancreatitis; lactic acidosis. | Cannot be taken with Retrovir (AZT) or Combivir (AZT + 3TC). |
| Hivid ® (ddC), by Hoffmann-La Roche (Nutley, NJ) | 0.75 mg every 8 hours | Peripheral neuropathy, nausea; mouth ulcers. | |
| Viread ™ (tenofovir DF), by Gilead Sciences (Foster City, CA) | 300 mg × 1/day | Nausea, vomiting, diarrhea, and flatulence. | If taken with ddI (Videx or Videx EC), it can increase ddI levels in the blood by as much as 60%, causing increased ddI side effects. |

[1]Long-term side effects of NRTIs. NRTIs have been associated with damage to the mitochondria. This damage may cause low red and white blood cell counts, muscle pain and wasting (particularly in the arms and legs), fatigue, peripheral neuropathy, and more rarely, serious liver (lactic acidosis) or pancreas problems.
*"x n" where n is an number, refers to administering the indicated dose n times a day.

TABLE 2

Protease inhibitors

| Drug | Adult dosing | Side effects[2] | Notes |
|---|---|---|---|
| Fortovase ® (saquinavir soft gel capsules), by Hoffmann-La Roche | 1600 mg × 2/day, or 1200 mg × 3/day | Nausea; diarrhea; stomach discomfort; insomnia; headache; increased liver enzyme levels | Should be administered within one hour after subject has ingested a meal containing at least 28 g fat. |
| Norvir ® (ritonavir), by Abbott Laboratories (Abbott Park, IL) | 600 mg × 2/day | Nausea; vomiting; diarrhea; loss of appetite; stomach discomfort; oral tingling and numbness; increased liver enzyme levels | High fat foods reduce side effects. Used at lower doses to enhance other protease inhibitors. |
| Crixivan ® (indinavir), by Merck & Co. | 800 mg every 8 hours | Kidney stones (seen in 6-8% of patients); nausea; vomiting; diarrhea; stomach discomfort; headache; insomnia; rash; back pain | Subject needs to take precautions against kidney stones, such as drinking at least 48 ounces water daily. |
| Viracept ® (nelfinavir), by Agouron Pharmaceuticals (San Diego, CA) | 750 mg × 3/day, or 1250 mg × 2/ day | Diarrhea; nausea; stomach discomfort; gas; rash; increased liver enzyme levels | Food encourages absorption. |
| Agenerase ® (amprenavir), by GlaxoSmithKline | 1200 mg × 2/day | Rash; diarrhea; nausea; vomiting; oral tingling and numbness | High-fat meals should be avoided. |
| Kaletra ® (lopinavir + ritonavir), by Abbott Laboratories | 1000 mg lopinavir/100 mg ritonavir × 2/day | Diarrhea; nausea; feeling week/tired; headache; pancreatitis | If combining with Sustiva ® (efavirenz), dose should be increased to 4 capsules, twice a day. |

[2]Long-term side effects of protease inhibitors. Use of protease inhibitors may be associated with changes in blood sugar levels (and rarely, development of diabetes), elevations in blood fat levels, and lipodystrophy. There have been reports of uncontrolled bleeding in hemophiliacs.

TABLE 3

Non-nucleoside reverse transcriptase inhibitors (NNRTIs)

| Drug | Adult dosing | Side effects | Notes |
|---|---|---|---|
| Viramune ® (nevirapine), by Roxane Laboratories (Columbus, OH) | 200 mg × 2/day | Rash; stomach upset; headaches; increased liver enzyme levels More rarely: hepatitis | |
| Rescriptor ® (delavirdine), by Agouron Pharmaceuticals | 400 mg × 3/day | Rash; headache; fatigue; stomach upset; elevated liver enzymes | |
| Sustiva ® (efavirenz), by Bristol-Myers Squibb | 600 mg × 1/day | Rash; drowsiness; insomnia; confusion; inability to concentrate; dizziness; vivid dreams; nausea; stomach discomfort; fever; insomnia; elevated liver enzymes. | Administration should be taken at bedtime to minimize dizziness, drowsiness and impaired concentration. |

SUMMARY

In a first aspect, the present invention is a compound of formula (XXIII), or pharmaceutically acceptable salts or esters thereof:

$$\begin{array}{c} R_4 \\ | \\ Q \end{array} \quad (XXIII)$$

$R_4$ is a nucleoside with Q substituting a 3' hydroxyl group, and Q is a moiety of formulas (XXIV)-(XXXII):

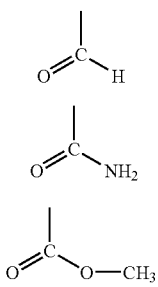

(XXIV)

(XXV)

(XXVI)

(XXVII)

(XXVIII)

(XXIX)

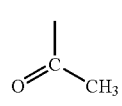

(XXX)

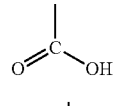

(XXXI)

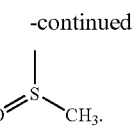

(XXXII)

In a second aspect, the present invention is a method of treating a subject infected with a retrovirus, comprising administering these compounds.

In a third aspect, the present invention is a method of inhibiting reverse transcriptase, comprising providing these compounds as substrates for the enzyme.

DETAILED DESCRIPTION

The present invention makes use of rational drug design and of the discovery that novel nucleoside analogs having structures with a branched 3'-group containing a carbon or sulfur central atom fit into the 3'-pocket of HIV RT, but do not bind to human DNA polymerases. These novel molecules act as substrates for RT, and like other nucleoside drugs, terminate reverse transcription prematurely. Unlike currently available nucleoside analogs, the molecules of the invention show greater specificity for RT compared to endogenous human DNA polymerases. These molecules take advantage of the tertiary structural differences between human DNA polymerases and HIV RT. A similar molecule (I) is ineffective in vivo; in that case, a nitrogen at the 3'-branched group proved ineffective (Hossain et al., 1993; Huang et al., 1995). Furthermore, these inhibitors are expected to be effective against RT of other retroviruses.

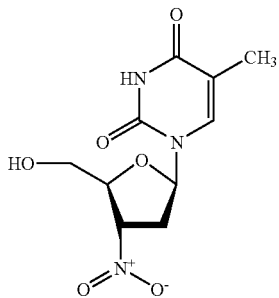

(I)

Figure 1:
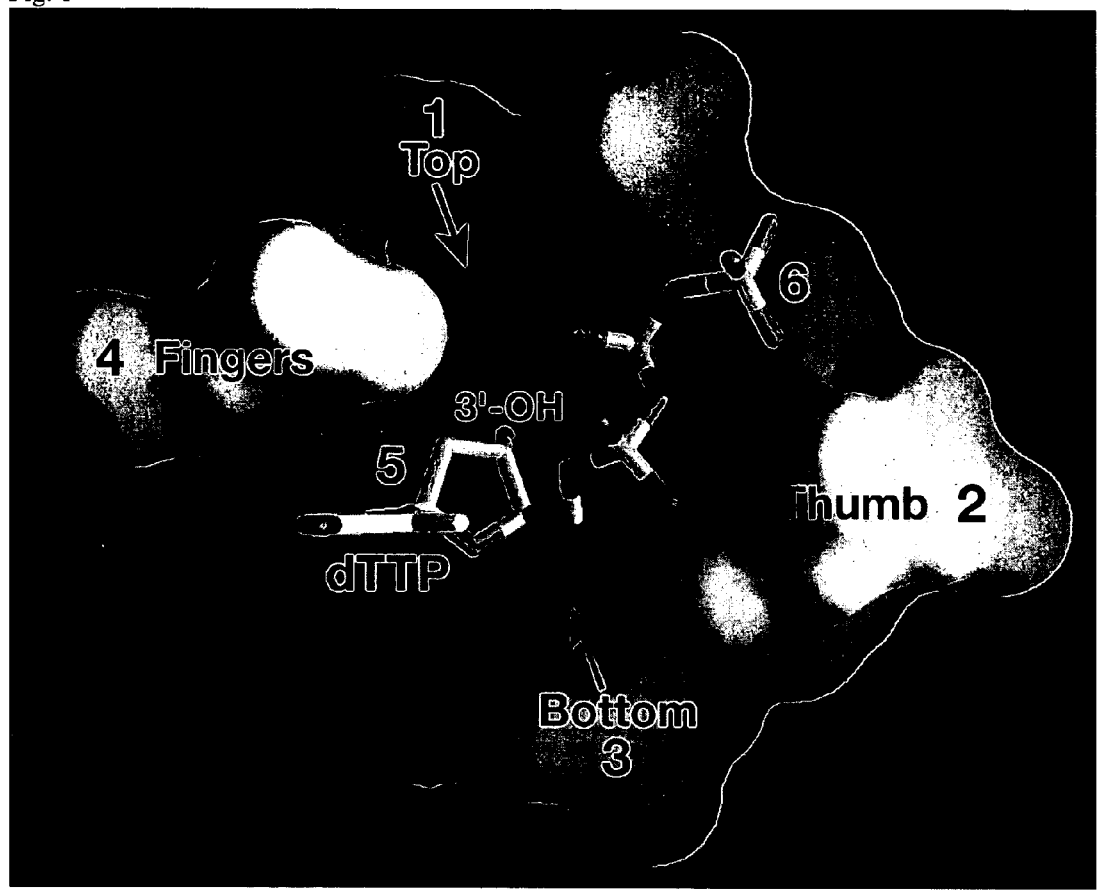
FIG. 1 shows the structure of polymerase active site in HIV reverse transcriptase.

Examining the crystal structure of ternary complexes of HIV RT covalently tethered via a disulfide bond to a DNA template at 3.2 Å (Huang et al., 1998) revealed, for the first time, the details of the dNTP binding site—where nucleoside analog inhibitors also bind (FIG. 1). Like most other DNA polymerases, HIV RT can be described as being a right hand, with a top 1, thumb 2, bottom (palm) 3 and fingers 4. When HIV RT forms a complex with a DNA template:primer and deoxythymidine triphosphate (dTTP), the dTTP occupies a cleft composed of part of the thumb 2 and fingers 4, with the palm 3 as the base. The 3'-hydroxyl group of the dTTP 5, which is modified in nucleoside analog drugs, projects into a pocket. The triphosphate portion 6 is also shown for orientation. Compared to that of human DNA polymerases, this "3'-pocket" is large, being able to accommodate an azido group like that of AZT-triphosphate (AZTTP). The large 3'-pocket is the critical difference that allows for specificity, where nucleoside inhibitors bind to HIV RT but not human DNA polymerases.

The azido group of AZTTP can occupy the large 3'-pocket either at the top 1 or bottom 3. A branched 3'-group with a sp2 central atom will fit into the entire 3'-pocket. Further considerations of the size limitation of the 3'-pocket leads to a structure (II):

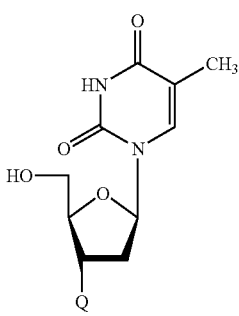

(II)

Where:
Q is a moiety of structure

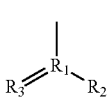

(III)

where
$R_1$ is C or S $R_2$ is H, F, $CH_3$, OH, $NH_2$ or a moiety of structure

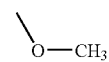

(IV)

$R_3$ is O, $CH_2$ or NH.

Eight members of this new class of nucleosides are of particular interest (V)-(XII):

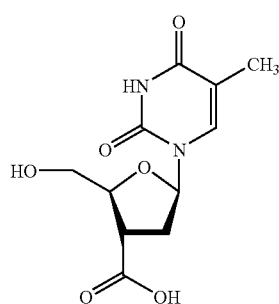

(V)

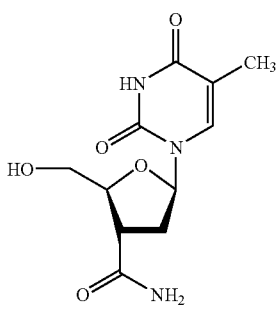

(VI)

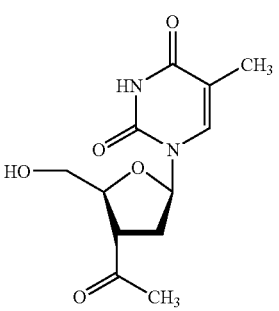

(VII)

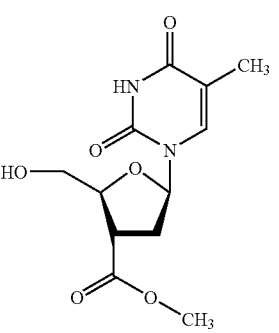

(VIII)

-continued (IX)
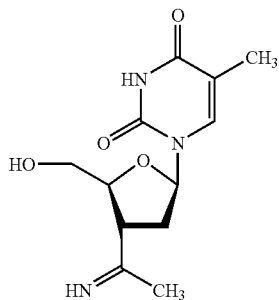

(X)
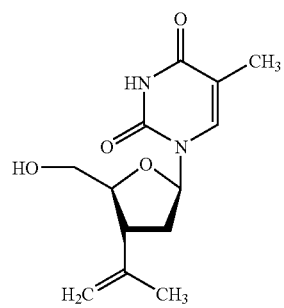

(XI)
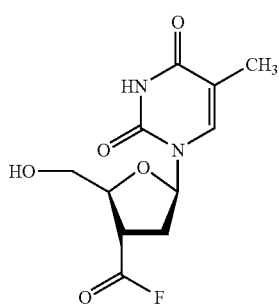

(XII)
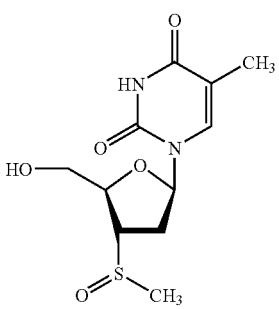

Q groups are shown in Table A (XXIV)-(XXXII).

In another embodiment, the novel nucleoside RT inhibitors have the general structure (XXIII):

(XXIII)
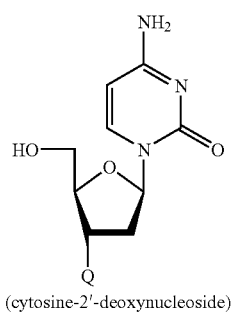

Where Q is a moiety of a structure of (III)
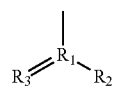

where $R_1$ is C or S $R_2$ is H, F, $CH_3$, OH, $NH_2$ or a moiety of structure (IV)
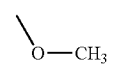

$R_3$ is O, $CH_2$, NH and $R_4$ is a naturally-occurring nucleoside, wherein the 3' hydroxyl group is substituted with the Q moiety (XIII)-(XVI):

(XIII)
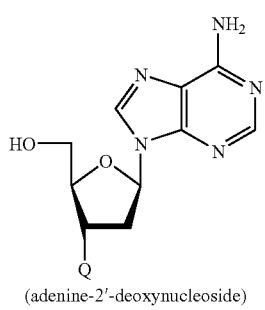
(adenine-2'-deoxynucleoside)

(XIV)
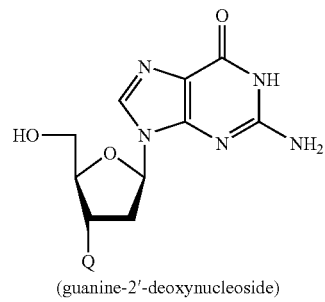
(guanine-2'-deoxynucleoside)

(XV)
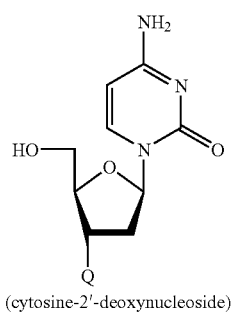
(cytosine-2'-deoxynucleoside)

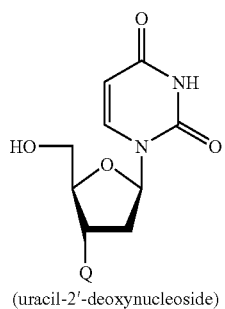

(uracil-2'-deoxynucleoside) (XVI)

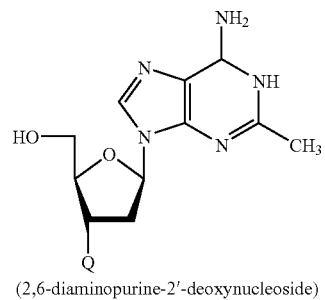

(2,6-diaminopurine-2'-deoxynucleoside) (XX)

In another embodiment, the $R_4$ is a universal (non-natural or natural) nucleoside, such as (XVII)-(XXII)

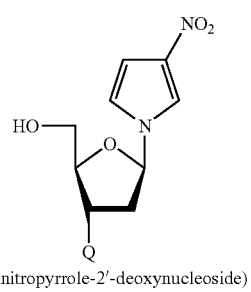

(3-nitropyrrole-2'-deoxynucleoside) (XVII)

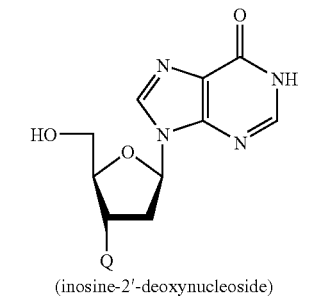

(inosine-2'-deoxynucleoside) (XXI)

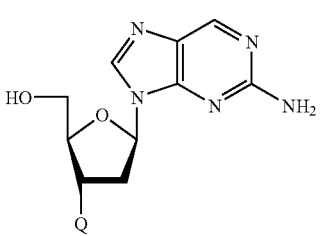

(2-aminopurine-2'-deoxynucleoside) (XXII)

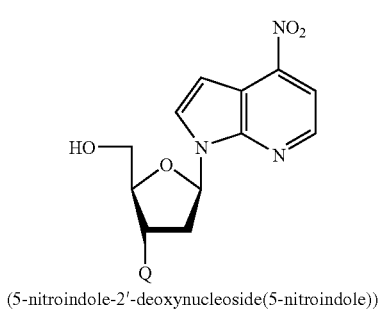

(5-nitroindole-2'-deoxynucleoside(5-nitroindole)) (XVIII)

(6H,8H-3,4-dihydropyrimido[4,5-c][1,2]oxazin-7-one-2'-dexoynucleoside(pyrimidine (C or T) analogue)) (XIX)

Q groups are shown in Table A (XXIV)-(XXXII).

TABLE A

Examples of moiety Q

 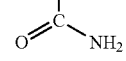

(XXIV) (XXV)

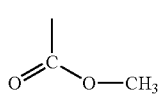 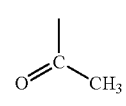

(XXVI) (XXVII)

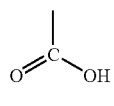 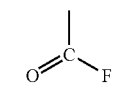

(XXVIII) (XXIX)

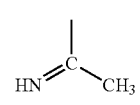 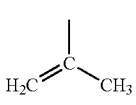

(XXX) (XXXI)

TABLE A-continued

Examples of moiety Q

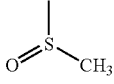

(XXXII)

These novel molecules inhibit HIV reverse transcriptase and represent new and important weapons in the molecular arsenal to combat the debilitating effects of HIV infection.

Definitions

Nucleosides

Nucleosides encompass bases conjugated to ribose and deoxyribose, yielding nucleosides and deoxynucleosides. Natural nucleosides are those that are found in DNA and RNA, such as the nucleosides that contain adenine, thymine, guanine, cytosine and uracil. Universal nucleosides refer to those that exhibit the ability to replace at least one of the natural nucleosides without significantly destabilizing neighboring base-pair interactions. Examples of universal nucleosides include 3-nitropyrrole 2'-deoxynucleoside, 5-nitroindole 2'-deoxynucleoside, 6H,8H-3,4-dihydropyrimido[4,5-c][1,2]oxazin-7-one-2'-deoxynucleoside, 2,6-diaminopurine-2'-deoxynucleoside, inosine-2'-deoxynucleoside and 2-aminopurine-2'-deoxynucleoside.

Synthesis of Novel Nucleoside Inhibitors of RT

Synthesis of Key Intermediate (XXXVII)

The inhibitors (V)-(XII) may be synthesized using standard chemical synthesis; reagents are generally available from Sigma-Aldrich (St. Louis, Mo.). For the synthesis of (V)-(XI), the intermediate (XXXVII) is first made (Table 4).

TABLE 4

Synthesis of intermediate (XXXVII)

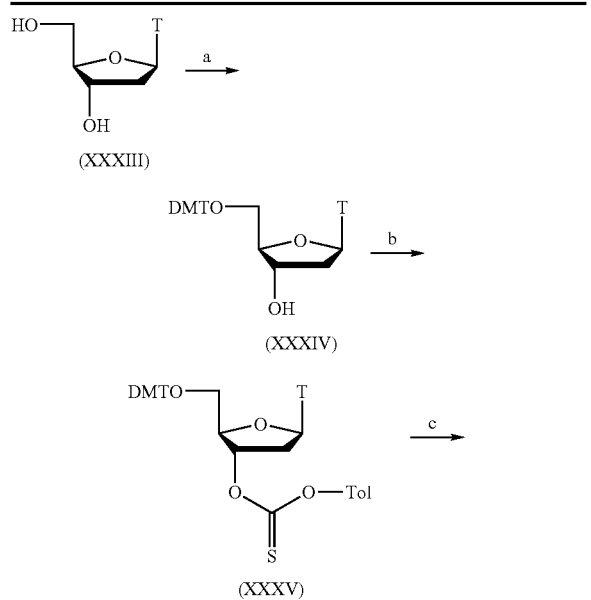

TABLE 4-continued

Synthesis of intermediate (XXXVII)

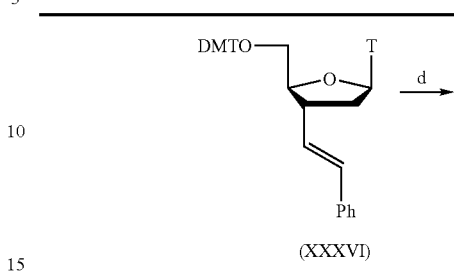

As an example describing the preparation of (XXXVII) (Table 4), 10 g of (XXXIII) (T, thymidine) is reacted with 10 g of 4,4'-dimethyoxytrityl chloride (DMTrCl) in the presence of 4-(dimethylamino)pyridine (DMAP) as a catalyst and pyridine as a solvent. After purification of the reaction mixture by column chromatography, 21 g of (XXXIV) (93% yield) is typically obtained as pale yellow foam. Reacting of 15 g of (XXXIV) with 7.7 g of O-(p-Tolyl) chlorothionoformate (TolOC(S)Cl) in the presence of DMAP, triethylamine, and methylene chloride, results in typically 16.6 g of (XXXV) (87% yield) after purification. Compound (XXXV) is converted into (XXXVI) by reacting with β-tributylstannyl styrene using 2,2'-azobis(2-methylpropionitrile) (AIBN) as a catalyst, affording typically 6.3 g of (XXXVI) (58% yield) after purification. The key intermediate (XXXVII) is obtained (typically 2.6 g, 30% yield) by oxidative cleavage of the double bond in (XXXVI) with $OsO_4/NaIO_4$.

Synthesis of (V) (Table 5)

As an example of preparing (V), 100 mg of (XXXVII) is reacted with $I_2$ in a mixture of acetonitrole and water, affording typically 95 mg of (XXXVIII) (93% yield) after purification. Deprotection of the DMT group in (XXXVIII) by treating with trichloroacetic acid ($CCl_3COOH$) in methylene chloride ($CH_2Cl_2$) typically results in 37 mg (98% yield) of (V). The scheme is depicted in Table 5.

TABLE 5

Synthesis of (V)

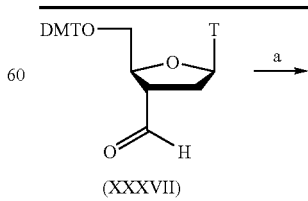

(XXXVII)

TABLE 5-continued

Synthesis of (V)

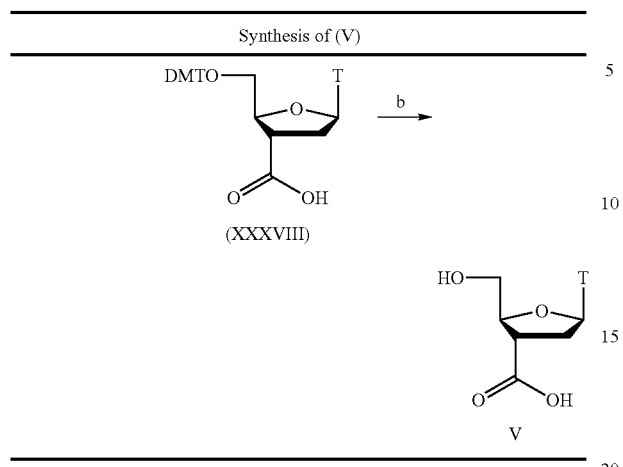

Synthesis of (VI) (Table 6)

As an example of preparing (VI), 100 mg of (XXXVII) is first treated with AIBN and N-bromosuccinimide (NBS) at 70° C. for two hours. The reaction mixture is cooled to 0° C., and the ammonia gas is bubbled through the mixture. Typically, 86 mg of (XXXIX) (84% yield) is recovered after purification by column chromatography. The same deprotection procedure used in the synthesis of (V) is applied to obtain typically 33 mg of (VI) from (XXXIX) (87% yield). The synthesis is shown in Table 6.

TABLE 6

Synthesis of (VI)

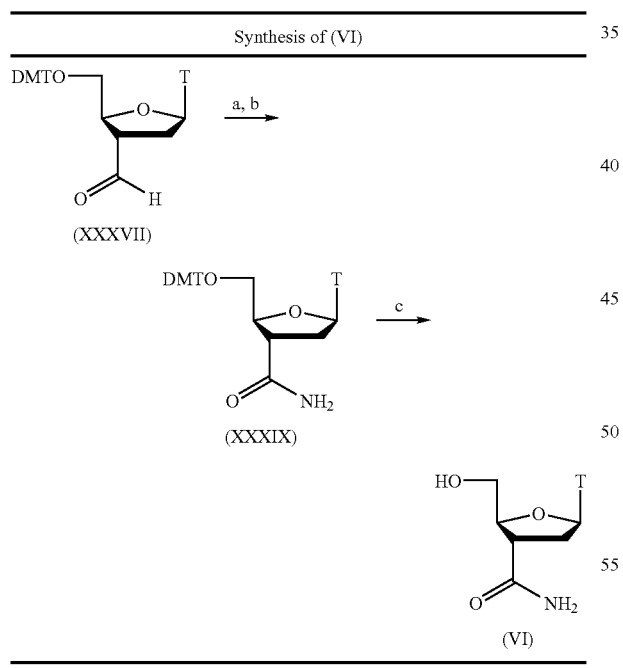

Synthesis of (VII) (Table 7)

As an example, 100 mg of (XXXVII) and cerium chloride (CeCl$_3$) are treated with methylmagnesium bromide (MeMgBr) at −10° C. for 3 hours. After working up, the obtained alcohol intermediate was treated with Dess-Martin reagent to yield 87 mg of (XLI) (85%), which was then deprotected as for (V), giving 36 mg of (VII).

TABLE 7

Synthesis of (VII)

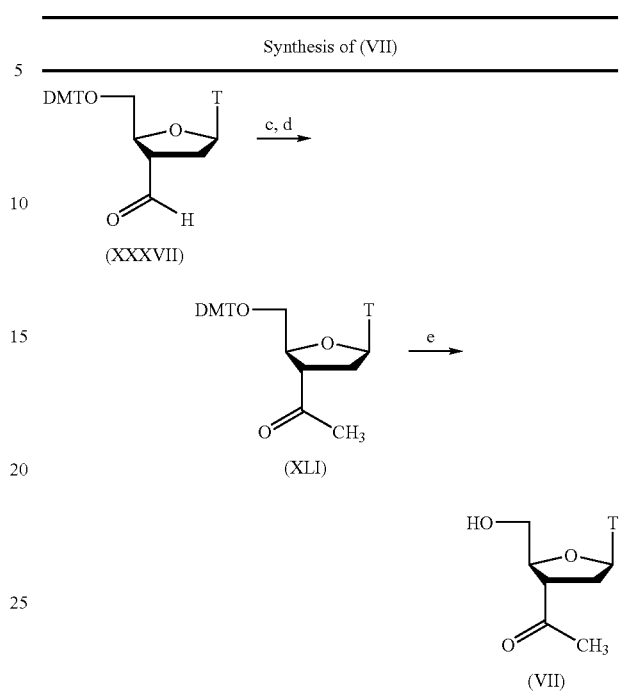

Synthesis of (VIII) (Table 8)

As an example, 100 mg of (XXXVII) is treated with I$_2$ in methanol at 0° C. to convert (XXXVII) to (XL) (typically 100 mg, 96% yield). Deprotection of DMT group in (XL) typically results in 46 mg of (VIII) (95% yield). The synthesis is shown in Table 8.

TABLE 8

Synthesis of (VIII)

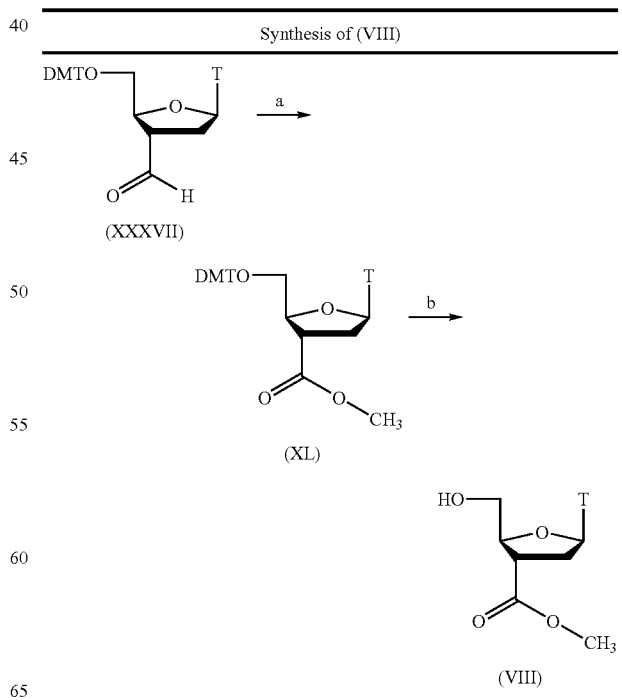

Synthesis of (IX) (Table 9)
The synthesis of (IX) is depicted in Table 9.
TABLE 9
Synthesis of (IX)
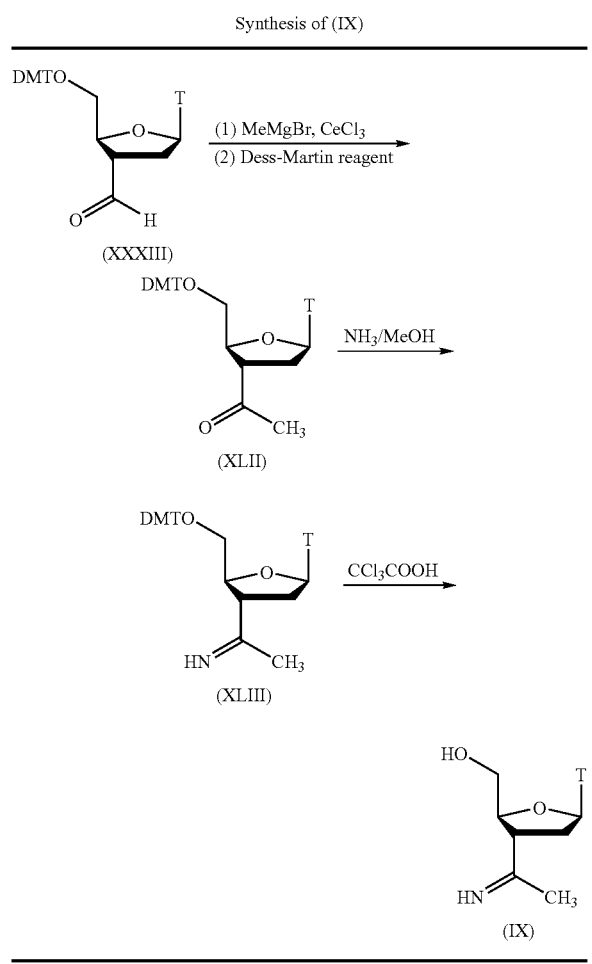
Synthesis of (X) (Table 10)
The synthesis of (X) is depicted in Table 10.
TABLE 10
Synthesis of (X)
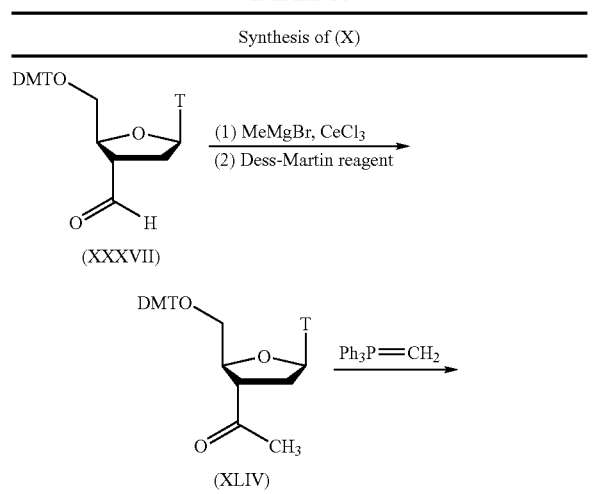
TABLE 10-continued
Synthesis of (X)
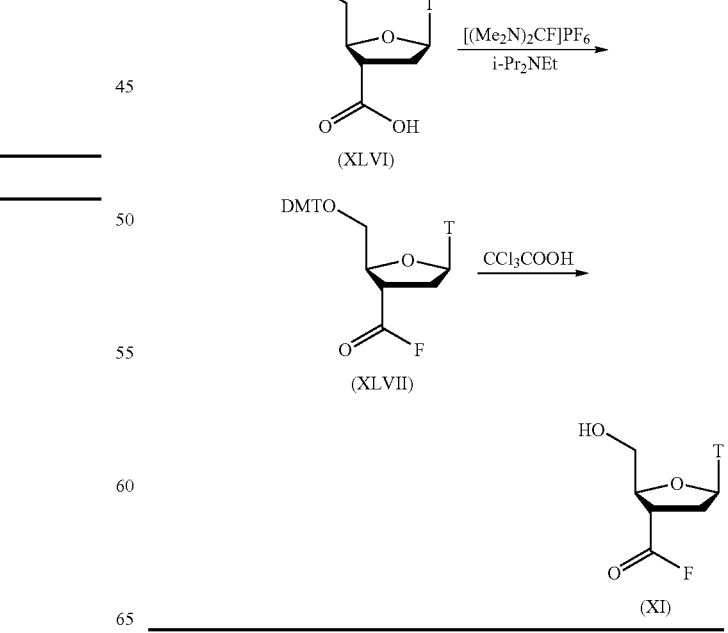
Synthesis of (XI) (Table 11)
The synthesis of (XI) is depicted in Table 11.
TABLE 11
Synthesis of (XI)
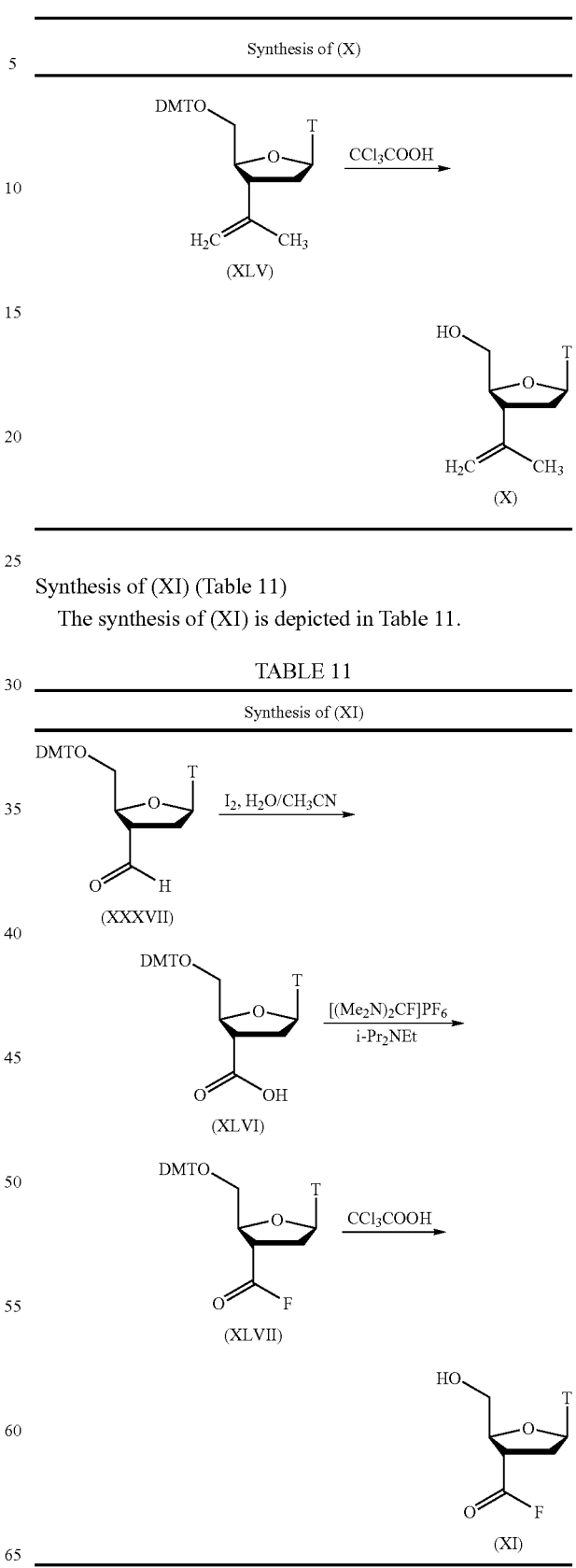

Synthesis of (XII) (Table 12)

The synthesis of (XII) is depicted in Table 12.

TABLE 12

Synthesis of (XII)

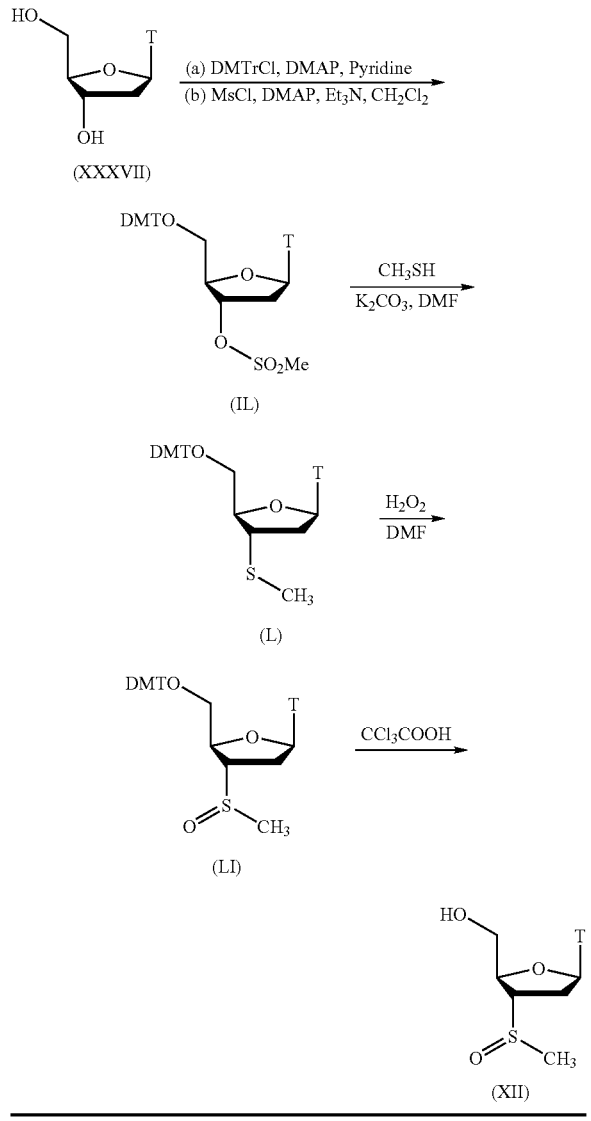

In the above examples, thymidine may be replaced with any other base.

Pharmaceutically acceptable salts, such as alkali metal, alkaline earth or ammonium salts, and esters, such as methoxy, ethoxy, 5'-monophosphate, 5'-diphosphate and 5'-triphosphate, of any of the RT inhibitors herein described are contemplated.

Pharmaceutical Compositions

The compounds of the invention, such as (V)-(XII), can be incorporated into pharmaceutical compositions. Such compositions typically comprise the compound and a pharmaceutically acceptable carrier. A "pharmaceutically acceptable carrier" includes solvents, dispersion media, coatings, antibacterial and antifungal agents, isotonic and absorption delaying agents, etc., compatible with pharmaceutical administration. Preferred examples of such carriers or diluents include water, saline, Finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

General Considerations

A pharmaceutical composition of the invention is formulated to be compatible with its intended route of administration, including intravenous, intradermal, subcutaneous, oral, inhalation, transdermal, transmucosal, and rectal administration. Solutions or suspensions used for parenteral, intradermal or subcutaneous application include sterile diluents for injection, such as water, saline, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide, if necessary. Parenteral preparations can be enclosed in ampules, disposable syringes or multiple dose vials made of glass or plastic.

Injectable Formulations

Pharmaceutical compositions suitable for injection include sterile aqueous solutions for water-soluble compounds, or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid for administration using a syringe. Such compositions should be stable during manufacture and storage and must be preserved against contamination from microorganisms, such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents, for example, parabens, chlorobutanol, phenol, ascorbic acid, and thimerosal, may be added. Isotonic agents, for example, sugars, polyalcohols such as manitol, sorbitol, and sodium chloride can be included in the composition. Compositions that can delay absorption include agents such as aluminum monostearate and gelatin.

Sterile injectable solutions can be prepared by incorporating the active compound (e.g., compounds (V)-(XII)) in the required amount in an appropriate solvent with one or a combination of ingredients as required, followed by sterilization. Generally, dispersions are prepared by incorporating the active compound into a sterile vehicle that contains a basic dispersion medium, and the other required ingredients. Sterile powders for the preparation of sterile injectable solutions, which methods of preparation include vacuum drying and freeze-drying to yield a powder containing the active compound and any desired ingredient from a sterile solution, may also be supplied.

Oral Compositions

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches, etc., can contain any of the following ingredients, or compounds of a similar nature: a binder, such as microcrystalline cellulose, gum tragacanth or gelatin; an excipient, such as starch or lactose; a disintegrating agent, such as alginic acid, PRIMOGEL, or corn starch; a lubricant, such as magnesium stearate or STEROTES; a glidant, such as colloidal silicon dioxide; a sweetening agent, such as sucrose or saccharin; or a flavoring agent such as peppermint, methyl salicylate, or orange flavoring.

Compositions for Inhalation

For administration by inhalation, the compounds are delivered as an aerosol spray from a nebulizer or a pressurized container that contains a suitable propellant, e.g., a gas such as carbon dioxide.

Transmucosal Transdermal Administration

Administration can also be transmucosal or transdermal. For transmucosal or transdermal administration, penetrants that can permeate the target barrier(s) are selected. Transmucosal penetrants include detergents, bile salts, and fusidic acid derivatives. Nasal sprays or suppositories can be used for transmucosal administration. For transdermal administration, the active compounds are formulated into ointments, salves, gels, or creams.

The compounds can also be prepared in the form of suppositories (e.g., with bases such as cocoa butter and other glycerides) or retention enemas for rectal delivery.

Carriers

In one embodiment, compounds (V)-(XII) are prepared with carriers that protect them against rapid elimination from the body, such as a controlled release formulations, implants and micro-encapsulated delivery systems. Biodegradable or biocompatible polymers can be used, such as ethylene vinyl acetate, polyanhydrides, polyglycolic acid, collagen, polyorthoesters and polylactic acid. Such materials can be obtained commercially from ALZA Corporation (Mountain View, Calif.) and NOVA Pharmaceuticals, Inc. (Lake Elsinore, Calif.). Liposomal suspensions can also be used as carriers. These can be prepared according to methods known to those skilled in the art, such as in (Eppstein et al., U.S. Pat. No. 4,522,811, 1985).

Unit Dosage

Oral formulations or parenteral compositions in unit dosage form can be created to facilitate administration and dosage uniformity. Unit dosage form refers to physically discrete units suited as single dosages for the subject to be treated, containing a therapeutically effective quantity of active compound, optionally in association with a pharmaceutical carrier.

In the treatment of a condition involving a RT, such as HIV infection, an appropriate dosage level will generally be 0.01 to 1000 mg per day that can be administered in single or multiple doses. More preferable, dosage will be between 60 mg to 500 mg, 100 mg to 400 mg and 200 mg to 300 mg/day. The total dosage per day may be administered once every 24 hours, or divided over 24 hours, such as into fourths (a quarter dose every 6 hours), thirds (⅓ dose every 8 hours) or halves (½ dose every 12 hours). An appropriate dosage level will generally be about 0.01 to 100 mg per kg patient body weight per day which can be administered in single or multiple doses. Preferably, the dosage level can be about 0.1 to about 75 mg/kg per day; more preferably about 0.5 to about 50 mg/kg per day.

Combinations of the novel compounds, or with any of those listed in Tables 1-3, may be administered to maximize RT inhibitory effects. For example, Trizivir® is a composite of AZT, 3TC and Ziagen®, and so too, may the compounds of the invention, such as compounds (V)-(XII) be administered in any combination with themselves, or other RT inhibitors. Additionally, these compounds may also be administered with anti-HIV proteases and non-nucleoside inhibitors of RT.

Some side effects may be diminished by adjusting dosing regimes, or having a subject take the pharmaceutical compositions during a meal or with certain foods, or not with a meal. Time of day of administration may also be adjusted to lessen side effects, such as administering a compound that induces insomnia early in the day.

Other Considerations in Treating Subjects Infected with a Retrovirus

Side effects of nucleoside RT inhibitors may include nausea, vomiting, stomach discomfort, loss of appetite, diarrhea, insomnia, muscle wasting, anemia, fatigue, peripheral neuropathy, rash, pancreatitis, lactic acidosis, mouth ulcers, and flatulence. Other longer-term side effects may include mitochondrial damage, which may cause low red and white blood cell counts, muscle pain and wasting, fatigue, peripheral neuropathy, lactic acidosis and pancreas problems. Also, some nucleoside inhibitors may not be combined, such as Zerit® and AZT.

Kits for Pharmaceutical Compositions

The pharmaceutical compositions can be included in a kit, container, pack, or dispenser together with instructions for administration. When the invention is supplied as a kit, the different components of the composition may be packaged in separate containers and admixed immediately before use. Such packaging of the components separately may permit long-term storage without losing the active components' functions. Such kits are exceptionally useful when mixing various compounds into a single composition would result in interaction and diminished potency.

(a) Containers or Vessels

The reagents included in kits can be supplied in containers of any sort such that the life of the different components are preserved, and are not adsorbed or altered by the materials of the container. For example, sealed glass ampules may contain lyophilized compounds (V)-(XII) or buffers that have been packaged under a neutral, non-reacting gas, such as nitrogen. Ampules may consist of any suitable material, such as glass, organic polymers, such as polycarbonate, polystyrene, etc., ceramic, metal or any other material. Other examples of suitable containers include simple bottles that may be fabricated from similar substances as ampules, and envelopes having foil-lined interiors, such as aluminum or an alloy. Other containers include test tubes, vials, flasks, bottles, syringes, etc. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

(b) Instructional Materials

Kits may also be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, laserdisc, audio tape, etc. Detailed instructions may not be physically associated with the kit; instead, a user may be directed to an internet web site specified by the manufacturer or distributor of the kit, or supplied as electronic mail.

EXAMPLES

The following examples are provided to illustrate the invention. Those skilled in the art can readily make insignificant variations in the compositions and methods of this invention. The examples are not meant to limit the invention in any way.

Example 1

Synthesis of RT Inhibitors (V)-(VIII)

The inhibitors (V)-(VIII) were synthesized using standard chemical synthesis; reagents are generally available from Sigma-Aldrich (St. Louis, Mo.).

Synthesis of Intermediate (XXXVII)

For the synthesis of (V)-(VIII), the intermediate (XXXVII) is first made (Table 4). Ten grams of (XXXIII) was reacted with 10 g of 4,4'-dimethyoxytrityl chloride (DMTrCl) in the presence of 4-(dimethylamino)pyridine (DMAP) as a catalyst and pyridine as a solvent. After purification of the reaction mixture by column chromatography, 21 g of (XXXIV) (93% yield) was obtained as pale yellow foam. Reacting of 15 g of (XXXIV) with 7.7 g of O-(p-Tolyl) chlorothionoformate (TolOC(S)Cl) in the presence of DMAP, triehylamine, and methylene chloride, gave 16.6 g of (XXXV) (87% yield) after purification. Compound (XXXV) was converted into (XXXVI) by reacting with β-tributylstannyl styrene using 2,2'-Azobis(2-methylpropionitrile) (AIBN) as a catalyst, affording 6.3 g of (XXXVI) (58% yield) after purification. The key intermediate (XXXVII) was obtained (2.6 g, 30% yield) by oxidative cleavage of the double bond in (XXXVI) with $OsO_4/NaIO_4$.

Synthesis of (V) (See Also Table 5)

One hundred mg of (XXXVII) is reacted with $I_2$ in a mixture of water and acetonitrile, yielding 95 mg of (XXXVIII) (93% yield) after purification. Deprotection of the DMT group in (XXXVIII) by treating with trichloroacetic acid ($CCl_3COOH$) in methylene chloride ($CH_2Cl_2$) typically gave 37 mg (98% yield) of (V).

Synthesis of (VI) (See Also Table 6) p One hundred milligrams of (XXXVII) was first treated with AIBN and N-Bromosuccinimide (NBS) at 70° C. for two hours. The reaction mixture was cooled to 0° C., and the ammonia gas was bubbled through the mixture. Eighty-six milligrams of (XXXIX) (84% yield) was recovered after purification by column chromatography. (XXXIX) was deprotected as for (V), obtaining 33 mg of (VI) from (XXXIX) (87% yield).

Synthesis of (VII) (See Also Table 7)

One hundred mg of (XXXVII) and cerium chloride ($CeCl_3$) was treated with methylmagnesium bromide (MeMgBr) at −10° C. for 3 hours. After working up, the obtained alcohol intermediate was treated with Dess-Martin reagent to yield 87 mg of (XLI) (85%), which was then deprotected as for (V), giving 36 mg of (VII).

Synthesis of (VIII) (See Also Table 8)

One hundred mg of (XXXVII) was treated with $I_2$ in methanol at 0° C. to convert (XXXVII) to (XL), yielding 100 mg (96% yield). Deprotection of DMT group in (XL) gave 46 mg of (VIII) (95% yield).

Example 2

Conversion of Nucleoside Analog Inhibitors to Their Corresponding Triphosphate Derivatives For primer extension experiments (Example 3), some of the novel nucleoside analog inhibitors were converted to triphosphate form in vitro, such as occurs in mammalian cells by endogenous enzymes. The corresponding triphosphate derivatives of (V)-(VII) are shown in Table 12.

Example 3

In vitro Demonstration for the Incorporation of Nucleoside RT Inhibitors (V)-(VII) into DNA by RT The suggested mechanism by which nucleoside RT inhibitors exert their effects requires their incorporation into growing DNA chains as they are reverse-transcribed from RNA. Once incorporated into the growing DNA strand, transcription is terminated because the nucleosides lack the necessary 3' hydroxyl group. This experiment demonstrates that the nucleoside analogs in their triphosphate forms (V)-(VII) are incorporated into growing DNA chains by RT.

The method is analogous to the Sanger sequencing. Specifically, in the presence of a template and four natural nucleotide triphosphates (dATP, dGTP, dCTP and dTTP), a radiolabeled primer is extended to full length by RT, as indicated by a single band on the sequencing gel. Addition of ddTTP, which competes with dTTP, results in the termination of primer extension at the positions of nucleotides opposite adenosine in the template strand. AZTTP, which is also a chain terminator, gives a similar result as ddTTP. If a compounds, e.g., (V) to (VII), in triphosphate form has a branched 3'-group that cannot be accommodated in the 3'-pocket of RT, the compound is not a substrate for RT. Therefore, it will be unable to compete with dTTP, resulting in a completed, extended product. However, if an added compound can productively occupy the active site and serve as a substrate of RT, like ddTTP and AZTTP, primer extension is blocked by the compound at positions opposite adenosine in the template.

If a chain terminator competes well, it is more probable that it is incorporated early during DNA synthesis, resulting in more lower molecular weight products, represented by relatively higher intensity of bands when the products are resolved using polyacrylamide or agarose gel electrophoresis. If a chain terminator competes poorly, more products with higher molecular weight are produced, resulting in relatively higher intensity of bands in the upper part of the gel. By varying the ratio of the natural nucleotides to the inhibitors, the relative kinetics of incorporation of new inhibitors, as compared to the current drugs, into DNA by RT and human DNA polymerase can be studied.

Figure 2:
FIG. 2 shows the results of an HIV reverse transcriptase inhibition primer extension experiment.

The results of such an experiment are shown in FIG. 2. Template cagatagtcttcacgaggcaggtcgtct-tgtcctggtActcgtttgcgttccg (SEQ ID NO:1) and primer gtctat-cagaagtgctccgtcc (SEQ ID NO:2) were used. With this template and primer, there is only one adenosine in the template to be read into the growing chain as a thymidine (capital and boldface in SEQ ID NO:1). If the tested compound is a substrate for RT, it will be incorporated into the growing chain at this position and the chain will prematurely terminate, giving a product 38 base pairs long instead of the full-length 53 base pairs. Compounds (C1) and (C2) were used as controls.

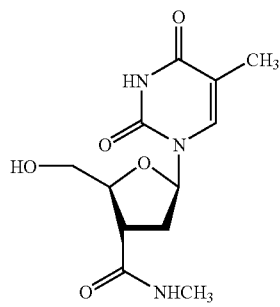

(C1)

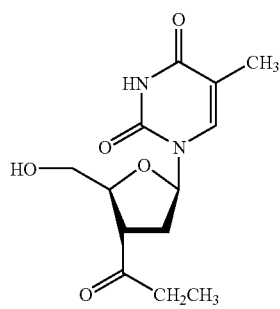

(C2)

Compounds (V) (lane 7), (VI) (lane 8) and (VII) (lane 9) were active, as indicated by the appearance of a band corresponding to the chain termination of the primer extension opposite the only A in the template. The efficiency of incorporation of these compounds by RT was roughly equivalent to ddTTP (lane 5) and AZTTP (lane 6), both also chain terminators. The assay did not show the appearance of the terminated products with control compounds, which possess larger 3'-groups (additional methylene groups; lanes 10 (C1) and 11 (C2)), indicating that they were not substrates for RT.

Example 4

In vitro Demonstration for Specificity: Nucleoside RT Inhibitors (V)-(XII) for RT Compared to Human DNA Polymerase (Prophetic Example)

The experiment of Example 4 is repeated but instead of RT, human DNA polymerase is used. Comparing these two experiments reveals the discrimination of inhibition of RT versus human DNA polymerase for ddTTP, AZTTP and XTP. A chain terminator, (ddTTP), competes against natural nucleotide, a dTTP in this case, for incorporation into DNA. The effectiveness of its ability to compete is reflected in relative distribution of terminated products.

TABLE 12

Conversion of nucleoside RT inhibitors to triphosphate forms in vitro

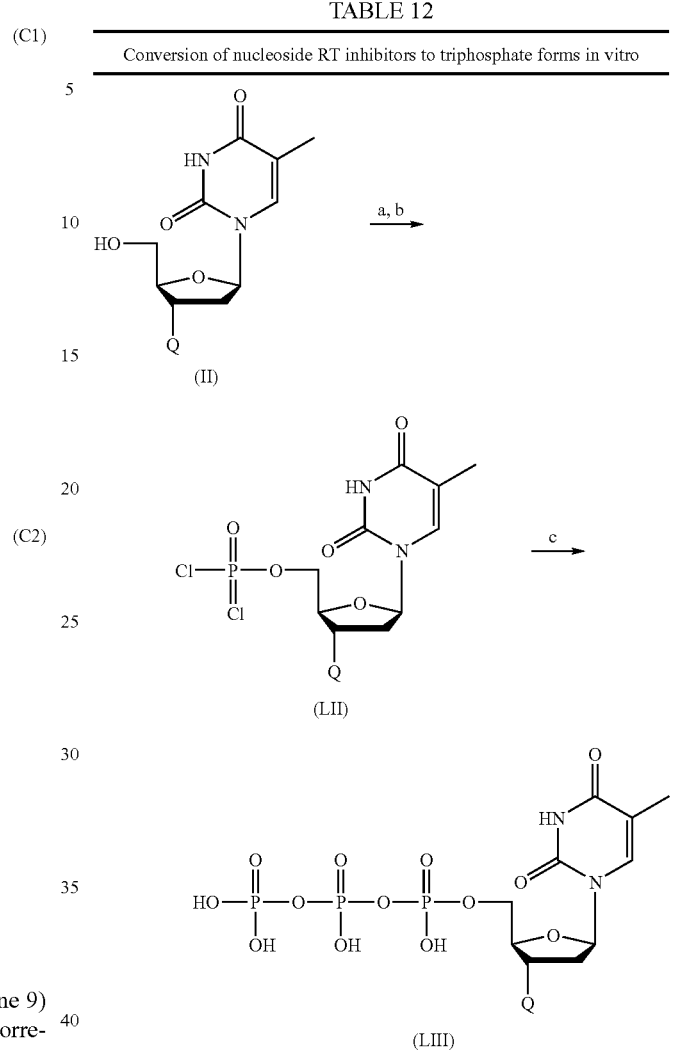

Reagents and conditions:
(a) POCl$_3$ pyridine;
(b) (Bu$_3$NH)$_2$H$_2$P$_2$O$_7$ and DMF;
(c) TEAB/H$_2$O.

Example 5

In vitro Demonstration for the Incorporation of Nucleoside RT Inhibitors into DNA by RT where the Base is Not Thymidine (Prophetic Example)

The suggested mechanism by which nucleoside RT inhibitors exert their effects requires their incorporation into growing DNA chains as they are reverse-transcribed from RNA. Once incorporated into the growing DNA strand, transcription is terminated because the nucleosides lack the necessary 3' hydroxyl group. This experiment demonstrates that the nucleoside analogs in their triphosphate forms, such as (VIII)-(XXII), are incorporated into growing DNA chains by RT.

In the presence of a template and four natural nucleotide triphosphates (dATP, dGTP, dCTP and dTTP), a radiolabeled primer is extended to full length by RT, as indicated by a single band on the sequencing gel. Addition of a chain inhibitor, such as ddATP, ddGTP, ddITP, ddCTP as controls, which compete respectively with dATP, dGTP, dITP and dCTP, results in the termination of primer extension at the positions of nucleotides opposite the corresponding complement in the template strand. If the candidate compound, e.g., (VIII)-(XXII) in triphosphate form has a branched 3'-group that cannot be accommodated in the 3'-pocket of RT, the compound is not a substrate for RT. Therefore, it will be unable to compete with the corresponding dNTP, resulting in a completed, extended product. However, if an added compound can productively occupy the active site and serve as a substrate of RT, like ddNTPs, primer extension is blocked by the compound at positions opposite adenosine in the template.

Example 6

In vivo Assay for Anti-HIV Activities of New Nucleoside Analogs Using an HIV-infected Cell Line (Prophetic Example)

Anti-viral susceptibility assays of these inhibitors on clinical isolates and drug resistant laboratory mutants will be performed. In vitro test of the inhibition of HIV replication by these new nucleoside analogs using an HIV infected cell-line will be carried out according to the method of Averett (1989).

REFERENCES

Averett, D. R. 1989. Anti-HIV compound assessment by two novel high capacity assays. *J. Virol. Meth.* 23:263-276.

Barre-Sinoussi, F., J. C. Chermann, F. Rey, M. T. Nugeyre, S. Chamaret, J. Gruest, C. Dauguet, C. Axler-Blin, F. Vezinet-Brun, C. Rouzioux, W. Rozenbaum, and L. Montagnier. 1983. Isolation of a T-lymphotropic retrovirus from a patient at risk for acquired immune deficiency syndrome (AIDS). *Science.* 220:868-71.

Beral, V., and R. Newton. 1998. Overview of the epidemiology of immunodeficiency-associated cancers. *J Natl Cancer Inst Monogr:* 1-6.

Eppstein et al., U.S. Pat. No. 4,522,811, 1985

Gallo, R. C., S. Z. Salahuddin, M. Popovic, G. M. Shearer, M. Kaplan, B. F. Haynes, T. J. Palker, R. Redfield, J. Oleske, B. Safai, and et al. 1984. Frequent detection and isolation of cytopathic retroviruses (HTLV-III) from patients with AIDS and at risk for AIDS. *Science.* 224:500-3.

Hossain, N., A. Papchikhin, N. Garg, I. Fedoriv and J. Chattopadhyaya. 1993. 208. Solution structure of lariat RNA by 500 MHz NMR spectroscopy and molecular dynamics studies in water. *Nucleosides & Nucleotides.* 12:499-528.

Huang, H., R. Chopra, G. L. Verdine, and S. C. Harrison. 1998. Structure of a covalently trapped catalytic complex of HIV-1 reverse transcriptase: implications for drug resistance. *Science.* 282:1669-75.

Huang, J. J., A. Rogouzeos and J. L. Rideout. 1995. A novel synthesis of 3'-deoxy-3'-nitrothymidine via nucleophilic substitution with nitrite anion. *J. Heterocyclic Chem.* 32:691-695.

Huang, P., D. Farquhar, and W. Plunkett. 1990. Selective action of 3'-azido-3'-deoxythymidine 5'-triphosphate on viral reverse transcriptases and human DNA polymerases. *J Biol Chem.* 265:11914-8.

Lin, T. S., and W. R. Mancini. 1983. Synthesis and antineoplastic activity of 3'-azido and 3'-amino analogues of pyrimidine deoxyribonucleoside. *J Med Chem.* 26:544-8.

Palella, F. J., Jr., K. M. Delaney, A. C. Moorman, M. O. Loveless, J. Fuhrer, G. A. Satten, D. J. Aschman, and S. D. Holmberg. 1998. Declining morbidity and mortality among patients with advanced human immunodeficiency virus infection. HIV Outpatient Study Investigators. *N Engl J Med.* 338:853-60.

Prevention, C.f.D.C.a. 1992. Centers for Disease Control and Prevention 1993 revised classification system for HIV infection and expanded surveillance case definition for AIDS among adolescents and adults. Morb. Mort. Week Report. 42:1-18.

Wei, X., S. K. Ghosh, M. E. Taylor, V. A. Johnson, E. A. Emini, P. Deutsch, J. D. Lifson, S. Bonhoeffer, M. A. Nowak, B. H. Hahn, and et al. 1995. Viral dynamics in human immunodeficiency virus type 1 infection. *Nature.* 373:117-22.

The invention claimed is:
1. A compound of formula (II) or (XIII-XXII) or pharmaceutically acceptable salts and esters thereof:
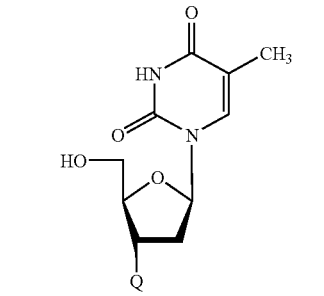
(II)
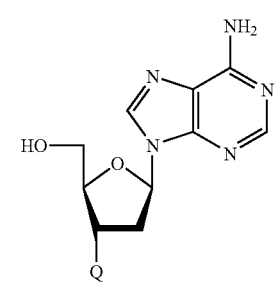
(XIII)
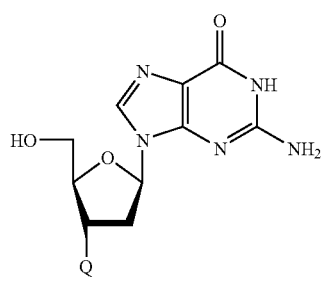
(XIV)
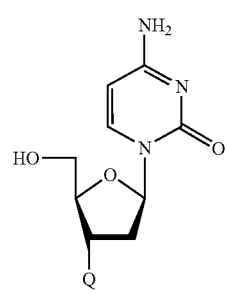
(XV)
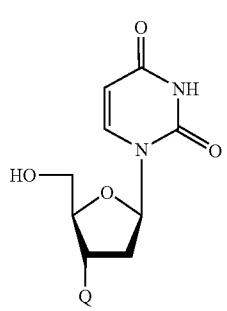
(XVI)
-continued
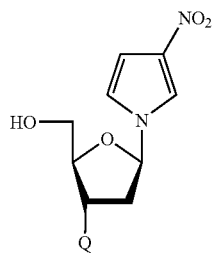
(XVII)
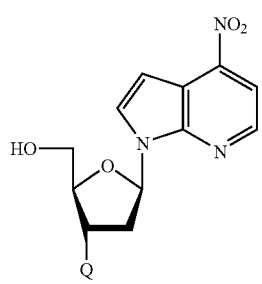
(XVIII)
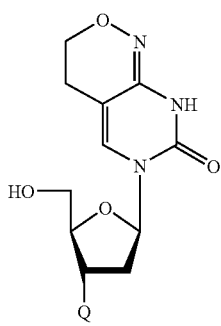
(XIX)
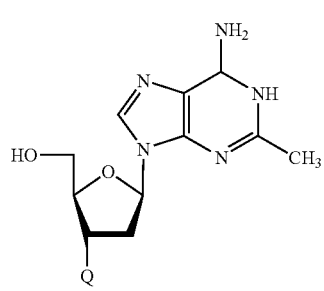
(XX)
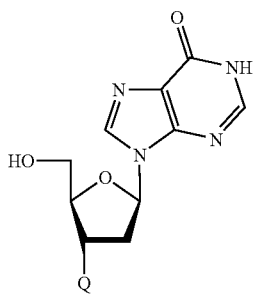
(XXI)

-continued
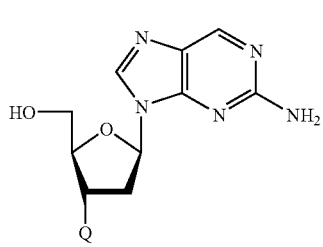
(XXII)
Wherein
Q is a moiety selected from the group consisting of moieties of formulas (XXV)-(XXXI):
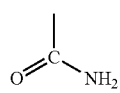
(XXV)
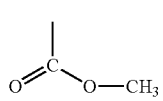
(XXVI)
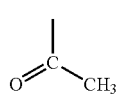
(XXVII)
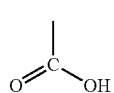
(XXVIII)
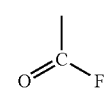
(XXIX)
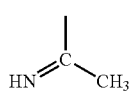
(XXX)
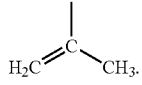
(XXXI)
2. A D-nucleoside selected from the group consisting of compounds of formulas (V)-(XI):
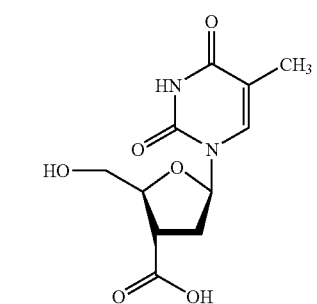
(V)
-continued
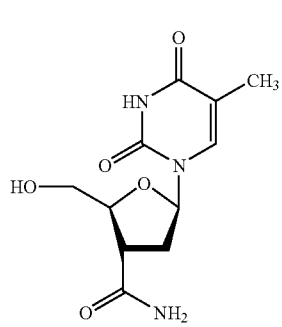
(VI)
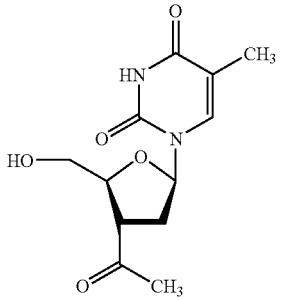
(VII)
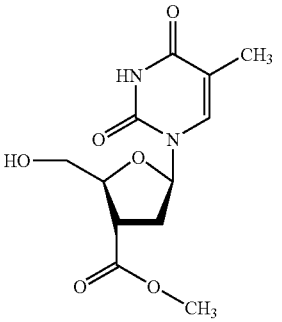
(VIII)
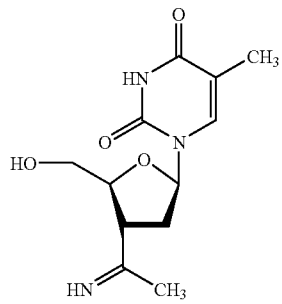
(IX)
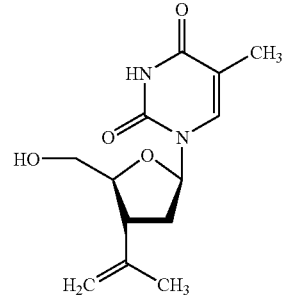
(X)

-continued

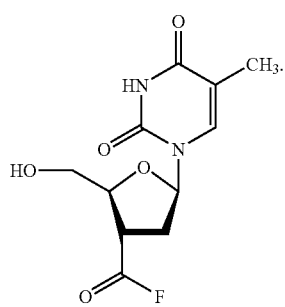
(XI)

3. The compound of claim 1, wherein the compound is in unit dosage form.

4. A method of treating a subject infected with a retrovirus, comprising administering to the subject the compound of claim 1.

5. The method of claim 4, wherein the retrovirus is a human immunodeficiency virus.

6. The method of claim 5, wherein the subject has acquired immune deficiency syndrome.

7. The compound of claim 2, wherein the compound is in unit dosage form.

* * * * *

SEQUENCE LISTING

```
<160> NUMBER OF SEQ ID NOS: 2

<210> SEQ ID NO 1
<211> LENGTH: 53
<212> TYPE: DNA
<213> ORGANISM: Artificial sequence
<220> FEATURE:
<223> OTHER INFORMATION: synthesized polynucleotide

<400> SEQUENCE: 1
cagatagtct tcacgaggca ggtcgtcttg tcctggtact cgtttgcgtt ccg         53

<210> SEQ ID NO 2
<211> LENGTH: 22
<212> TYPE: DNA
<213> ORGANISM: Artificial sequence
<220> FEATURE:
<223> OTHER INFORMATION: synthesized polynucleotide

<400> SEQUENCE: 2
gtctatcaga agtgctccgt cc                                            22
```